United States Patent [19]
Voorhees et al.

[11] Patent Number: 5,998,394
[45] Date of Patent: Dec. 7, 1999

[54] COMPOSITIONS FOR TREATING SKIN CONDITIONS BY ENHANCING THE ACTIVITY OF 1,25(OH)$_2$D$_3$ USING AN RXR LIGAND AND/OR A 24-HYDROXYLASE INHIBITOR

[76] Inventors: John J. Voorhees; Sewon Kang, both of Dept. of Dermatology, University of Michigan 1910 Taubman Center, Ann Arbor, Mich. 48109; Geert Cauwenbergh, Johnson & Johnson Consumer Products Worldwide, Skillman, N.J. 08558

[21] Appl. No.: 09/078,260

[22] Filed: May 13, 1998

Related U.S. Application Data

[62] Division of application No. 08/832,865, Apr. 4, 1997
[60] Provisional application No. 60/015,145, Apr. 5, 1996.
[51] Int. Cl.$^6$ .......................... A61K 31/59; A61K 31/495
[52] U.S. Cl. ............................................ 514/167; 514/252
[58] Field of Search ...................................... 514/167, 252

[56] References Cited

U.S. PATENT DOCUMENTS 4,569,935  2/1986  Rosenberg et al. ...................... 514/252

OTHER PUBLICATIONS

Spearman et al., Brit. J. Dermatology, 40(5) 553–60 (abstract), 1974.

Lutzow–Horn et al., Experimental Dermatology 2(3), 113–20 (Denmark) (abstract), 1993.

*Primary Examiner*—James H. Reamer
*Attorney, Agent, or Firm*—Hopgood, Calimafde, Kalil & Judlowe

[57] ABSTRACT

Described are in vivo methods for testing the activity of vitamin D$_3$ (1,25-dihydroxyvitamin D$_3$) and analogs thereof in human skin and for testing the effect of a test compound on said activity. Also described are methods for enhancing the in vivo activity of vitamin D$_3$ and analogs thereof by coadministering vitamin D$_3$ or an analog thereof with an RXR ligand, a 24-hydroxylase inhibitor, or a mixture thereof. Preferred RXR ligand materials are retinoids, such as 9-cis retinoic acid, and precursors thereof, such as all trans retinoic acid. Preferred 24-hydroxylase inhibitors are imidazoles, especially those inhibiting cytochrome-P450 oxidative enzymes, such as ketoconazole. Also included is a method for determining whether a candidate compound inhibits 24-hydroxylase activity or induction thereof.

16 Claims, 8 Drawing Sheets

COMPOSITIONS FOR TREATING SKIN CONDITIONS BY ENHANCING THE ACTIVITY OF 1,25(OH)$_2$D$_3$ USING AN RXR LIGAND AND/OR A 24-HYDROXYLASE INHIBITOR

This application is a division of Ser. No. 08/832,865 filed Apr. 4, 1997. This application claims priority from provisional application Ser. No. 60/015,145, filed Apr. 5, 1996, the disclosure of which is incorporated herein by reference.

TECHNICAL FIELD

This invention relates especially to the molecular action of 1,25-dihydroxyvitamin D3 (1,25(OH)$_2$D$_3$). More particularly it relates to assays for determining vitamin D activity in skin, to methods for enhancing the therapeutic use of 1,25(OH)$_2$D$_3$ (and its analogs), and for increasing the safety and/or effectiveness of using 1,25(OH)$_2$D$_3$ in treatments for skin conditions.

BACKGROUND

Vitamin D3 was discovered as a result of efforts to determine the nutritive factor responsible for the antirachitic property (i.e., ability to prevent rickets) of cod liver oil. Vitamin D3 (also called cholecalciferol) is photosynthesized from 7-dehydroxycholesterol (previtamin D3) in skin by UV-induced cleavage of the carbon-carbon bond between C9 and C10, enters circulation, and binds to vitamin D binding protein (DBP) for transport. DBP-bound vitamin D3 is biologically inert and requires activation. In the liver vitamin D3 is hydroxylated at the C-25 position by a cytochrome P-450 enzyme system to monohydroxyvitamin D$_3$, 25(OH)D$_3$, the major circulating form of vitamin D. This metabolite is hydroxylated again in the kidney at the C-1 position to form dihydroxyvitamin D$_3$, 1,25(OH)$_2$D$_3$, the hormonally active vitamin D metabolite. Dihydroxyvitamin D$_3$ is metabolized by 24-hydroxylase at the C-24 position to form 1,24,25-trihydroxyvitamin D3 (1,24,25 (OH)$_3$D$_3$), which is biologically inert. The trihydroxyvitamin D$_3$ is ultimately metabolized to calcitroic acid. In vitro studies of the metabolism of 1,25(OH)$_2$D$_3$ indicate that it catalyzes its own catabolism, but a mechanism therefor has not been suggested. Ray, S., et al., J. Cell Biochem (1995) 59:117–122.

The cellular receptor for 1,25(OH)$_2$D$_3$ (designated VDR, for Vitamin D Receptor) is a member of family II of the hormone receptor superfamily of transcription factors. VDR has been fully characterized and is primarily localized in the nuclear compartment of the cell. In the cell nucleus, VDR, in the presence of 1,25(OH)$_2$D$_3$, heterodimerizes with the retinoid X receptor (RXR). This dimeric complex binds to a vitamin D responsive element (VDRE, characterized by direct repeats of the hexamer AGGTCA spaced by three nucleotides) and activates vitamin D responsive genes.

9-cis retinoic acid is the native ligand for RXR. Its effect in vivo on the above-described intracellular action of 1,25 (OH)$_2$D$_3$ is not known.

1,25(OH)$_2$D$_3$'s antirachitic activity is based on its enhancement of intestinal absorption of dietary calcium and its mobilization of calcium stores from bone. More recently it has been found to decrease proliferation and increase terminal differentiation of human keratinocytes, and to exhibit immunosuppressive activity on Th$_1$ cells. These findings have led to its use to treat dermatological disorders such as psoriasis. The use of 1,25(OH)$_2$D$_3$ to treat dermatological disorders is tempered, however, by its potent calcemic effects. Those effects have led to the development of 1,25(OH)$_2$D$_3$ analogs, such as calcipotriene, that have reduced calcemic effects. Even so, the search continues for ways to improve the therapeutic efficacy of 1,25(OH)$_2$D$_3$ and its analogs in dermatology.

SUMMARY OF THE INVENTION

The present invention provides novel methods for assessing the 1,25(OH)$_2$D$_3$ activity of a test compound, and whether a test compound can enhance the activity of 1,25 (OH)$_2$D$_3$ (or an active analog thereof). It also provides methods for improving the therapeutic efficacy of 1,25(OH)$_2$D$_3$ and its analogs.

The present invention is primarily based on two scientific findings. The first is that the 24-hydroxylase gene, which contains a VDRE, is present in skin and is activated by 1,25(OH)$_2$D$_3$ in vivo. Thus, indicia of such activation, such as 24-hydroxylase mRNA induction and 24-hydroxylase production, are sensitive markers of vitamin D activity in vivo. This finding has also led to the discovery of this invnetion, that 24-hydroxylase inhibitors can increase vitamin D activity in vivo. The second is that the RXR ligand enhances the intracellular action of 1,25(OH)$_2$D$_3$ in vivo.

Accordingly, one aspect of the present invention is an in vivo method for determining whether a candidate (test) compound exhibits 1,25(OH)$_2$D$_3$ activity in skin, which method comprises applying the test compound to living skin, determining the amount of 24-hydroxylase mRNA or 24-hydroxylase in the skin following the topical application of the test compound, and comparing the concentration determined (of mRNA or the hydroxylase) to a control; an increase in the amount of 24-hydroxylase mRNA or 24-hydroxylase in the skin relative to the control indicates the compound has 1,25(OH)$_2$D$_3$ activity in skin.

Another aspect of the invention is an in vivo method for determining the effect of a candidate (test) compound on the activity of 1,25(OH)$_2$D$_3$ or an analog thereof (or mixtures thereof) in skin (i.e., in vivo) which comprises applying 1,25(OH)$_2$D$_3$ or an analog thereof (or mixtures thereof) both with and without coapplication of the test compound to separate areas of living skin, determining the amount of 24-hydroxylase mRNA or 24-hydroxylase in each of the separate skin areas following the application of the compound, and comparing the amounts determined; a larger amount of 24-hydroxylase mRNA or 24-hydroxylase in the skin to which both 1,25(OH)$_2$D$_3$ (or said analog) and the test compound were applied indicates that the test compound enhances the activity of 1,25(OH)$_2$D$_3$ (or the analog) in living skin.

Yet another aspect of the invention is a method of treating a dermatological disorder characterized at least in part by hyperproliferation or hypodifferentiation of keratinocytes, or of inflammation, in a human patient, which comprises topically coadministering to the area of skin of the patient affected by said disorder an amount of (a) 1,25(OH)$_2$D$_3$ (or an analog thereof) and (b) at least one of an RXR ligand and a 24-hydroxylase inhibitor, wherein the combined amount is effective to ameliorate one or more dermatological symptoms of the disorder. In preferred embodiments, the method comprises apply 1,25(OH)$_2$D$_3$, an RXR ligand, and a 24-hydroxylase inhibitor.

In yet another aspect this invention provides a method or improving the safety and/or effectiveness of using an amount of 1,25(OH)$_2$D$_3$ effective for the treatment of a dermatological disorder, which comprises reducing the amount of 1,25)OH)$_2$D$_3$ applied and administering therewith at least one of an RXR ligand and a 24-hydroxylase inhibitor. By decreasing the amount of dihydroxyvitamin $D_3$ required in such treatments, hypercalcemia and other undesirable effects thereof can be reduced because less of the vitamin is administered, thus improving the safety of such treatment. Viewed another way, a lesser amount of dihydroxyvitamin $D_3$ can be used when co-administered with an RXR ligand and/or a 24-hydroxylase inhibitor because the latter essentially increase the effectiveness of the lesser amount of the dihydroxyvitamin $D_3$ applied.

In still another aspect, the invention provides a method for determining whether a candidate compound inhibits 24-hydroxylase activity, which comprises inducing 24-hydroxylase activity in vivo in skin, biopsying skin cells in which the 24-hydroxylase was induced, dividing the biopsied cells into two groups, adding a tagged monohydroxyvitamin $D_3$ to a first group of cells and thereafter measuring the amount of tagged dihydroxyvitamin $D_3$, adding a tagged monohydroxyvitamin $D_3$ plus the candidate compound to a second group of cells and thereafter measuring the amount of tagged dihydroxyvitamin $D_3$, wherein a lesser amount of tagged dihydroxyvitamin $D_3$ in the second group tested indicates inhibition of 24-hydroxylase activity or induction thereof.

DESCRIPTION OF PREFERRED
EMBODIMENTS OF THE INVENTION

As used herein the term "$1,25(OH)_2D_3$ activity in skin" intends the ability to decrease proliferation and/or increase terminal differentiation of human keratinocytes.

As used herein the term "$1,25(OH)_2D_3$ analog" intends a compound that possesses $1,25(OH)_2D_3$ activity. Such analogs generally are structurally related to $1,25(OH)_2D_3$, such as, without limitation, calcipotriene, and those disclosed in U.S. Pat. Nos. 5,087,619, 5,145,846, 5,342,833, 5,403,832, 5,428,029 and 5,451,574, EPA Pub. No. 0398217B1, and PCT Pub. No. WO 95/01960, the disclosures of which are incorporated herein by reference.

As used herein, terms such as "co-application", "co-administering", and the like are intended to mean that the compounds are applied to the skin at relative times such that their actions are cooperative; preferably, the compounds are applied with a few hours of each other, more preferably the compounds are applied sequentially, and most preferably the compounds are applied simulataneously (e.g., in the same physical formulation).

As indicated above the invention contemplates in vivo methods for screening candidate compounds to determine whether such compounds (a) possess $1,25(OH)_2D_3$ activity in skin and (b) enhance $1,25(OH)_2D_3$ activity in skin.

When screening a compound to determine whether it possesses $1,25(OH)_2D_3$ activity in skin, the compound is first applied topically to skin. Normally the compound will be applied in the form of an ointment or lotion at one or more concentrations (usually between 0.001% to 0.1% by weight). A predetermined volume of the formulation is applied to a predetermined area of skin of normal healthy adults. The application site(s) is occluded with an appropriate dressing for a predetermined time period, usually 2 to 4 days. Biopsy samples of the treated skin and untreated (control) skin are then taken and processed to obtain nuclear or protein extracts, and the extracts can be subjected to Northern blot or biochemical enzyme activity analysis (e.g., as described below) to determine its 24-hydroxylase mRNA amount (concentration) or 24-hydroxylase activity.

When screening a compound to determine whether it enhances $1,25(OH)_2D_3$ activity in skin, the compound is co-applied to the skin with $1,25(OH)_2D_3$ or an analog thereof as above. $1,25(OH)_2D_3$ (or analog) will typically be applied at a concentration between about 0.001% to 0.1% by weight. Skin treated only with $1,25(OH)_2D_3$ (or analog) is used as a control (i.e., without co-application). After occluding the skin areas to which application of the compound(s) was made, the 24-hydroxylase mRNA concentration or 24-hydroxylase activity of the treated skin is determined as described above.

The 24-hydroxylase mRNA content and 24-hydroxylase activity of normal, untreated skin is barely detectable. Various examples following illustrate the levels of elevation in $1,25(OH)_2D_3$ that result from treating skin with a combination of the dihydroxyvitamin $D_3$ and a 24-hydroxylase inhibitor.

Examples of 24-hydroxylase inhibitors are ketoconazole and other dermatologically acceptable azoles or imidazoles that inhibit cytochrome-P450 oxidative enzymes. Still further, analytical methods described below explain both testing for 24-hydroxylase activity (or 24-hydroxylase mRNA concentration) and testing for whether a particular test compound inhibits the activity (whether the mode of inhibition is direct or through inhibiting the transduction pathway).

As indicated above, the invention also contemplates using RXR ligands instead of and in addition to 24-hydroxylase inhibitors to increase the activity of $1,25(OH)_2D_3$ or analogs thereof in living skin. Such ligands and/or inhibitors are coadministered with $1,25(OH)_2D_3$ or an analog thereof When an analog is used in combination with a 24-hydroxylase inhibitor in practicing the present methods, the analog must be a substrate for 24-hydroxylase (e.g., the analog must be metabolized by 24-hydroxylase into an inactive metabolite).

Examples of RXR ligand materials (also termed "RXR ligands" herein) that are suitable for used the methods of this invention include, without limitation, 9-cis retinoic acid and the RXR ligands described in PCT Pubs. Nos. WO 93/03713, WO 93/21146, WO 94/15902 and WO 95/04036, the disclosures of which are incorporated herein by reference. Precursors that result in 9-cis retinoic acid (e.g. all trans retinoic acid) may also be used as the RXR ligand material.

The $1,25(OH)_2D_3$ or analog and the RXR ligand and/or 24-hydroxylase inhibitor can be formulated for topical administration to skin either separately or combined together in a mixture. As used herein, the term "topical" denotes the use of $1,25(OH)_2D_3$/analog, RXR ligand/24-hydroxylase inhibitor, incorporated in an acceptable dermatological carrier, and applied at the affected skin site for the exertion of local action.

Accordingly, the topical compositions include those pharmaceutical forms in which the compound is applied externally by direct contact with the skin. The topical dosage preparations comprise gels, creams, lotions, ointments, powders, aerosols, soaps, and other conventional forms for applying medication to the skin by admixing the active ingredients with known pharmaceutical topical carrier materials and adjuvants. Ointments and creams encompass formulations having oleaginous, absorbable, water-soluble, and emulsion-type bases such as petrolatum, lanolin, polyethylene glycols and the like. Lotions are liquid preparations and vary from simple solutions to aqueous or hydroalcoholic preparations containing finely divided substances. Lotions typically contain suspending or dispersing agents, such as cellulose derivatives (ethyl cellulose, methyl cellulose, and the like), gelatin, or gums, and incorporate the active ingredient(s) in a vehicle of water, alcohol, glycerin and the like. Gels are semi-solid preparations made by gelling a solution or suspension of the active ingredients in a carrier vehicle. The vehicles, which can be hydrous or anhydrous, are gelled using a gelling agent, such as, carboxypolymethylene, and neutralized to a proper gel consistency with the use of alkaline compounds, such as sodium hydroxide and amines. Soaps (such as NIZORAL® brand of ketoconazole, provided as a 2% cream and a 2% shampoo) can be formulated as solids (such as bars) or a liquids (such as shampoo) including conventionally used surfactants, foaming agents, fragrances, and the like. All topically applied compositions can include one or more compatible adjuvants conventionally used in topically applied compositions, such as colorants, fragrances, humectants, demulcents, and the like, and mixtures thereof that are compatible with each other as well as with the active ingredients.

The therapeutic method of the invention may be used to treat skin diseases associated with hyperproliferation or hypodifferentiation of epidermal cells or inflammation such as psoriasis, actinic keratoses (precancerous lesions typically caused by chronic UV exposure), disorders of keratinization such as ichthyoses and keratoses, and sebaceous gland diseases such as acne or seborrheic dermatitis. In these methods, the $1,25(OH)_2D_3$ or analog will normally be administered daily topically in formulations having concentrations ranging between 0.002% to about 0.05% (by weight) of the dihydroxyvitamin $D_3$. Correlatively, the RXR ligand will normally be coadministered at concentrations of about 0.025% to 0.1% (depending upon potency) and the 24-hydroxylase inhibitor is coadministered at about 1% to 3% (depending on potency) daily. Thus, it should be understood that one aspect of this invention is enhancing the treatment of a dermatological condition which is treated with high doses of $1,25(OH)_2D_3$ by decreasing the effective amount of dihydroxyvitamin $D_3$ administered and coadministering therewith a 24-hydroxylase inhibitor, an RXR ligand, or a combination of both (i.e., a composition comprising dihydroxyvitamin $D_3$, a 24-hydroxylase inhibitor, and an RXR ligand). The coadministration of the inhibitor and/or the ligand provides a safer treatment, by reducing the effective amount of dihydroxyvitamin $D_3$ required to treat the condition, thereby reducing potential hypercalcemia, and provides a more effective treatment, by enabling the use of a lower dose of the dihydroxyvitamin $D_3$.

The methods of this invention are further illustrated by the following examples. These examples are not intended to limit the invention in any manner. Following, "24-OHase" means '24-hydroxylase'.

Example 1

Effect on $1,25(OH)_2D_3$ in Skin of 9-Cis Retinoic Acid Topical Application

Solutions of $1,25(OH)_2D_3$ (0.002%, 0.05%), 9-cis retinoic acid (0.1%) and $1,25(OH)_2D_3$ plus 9-cis retinoic acid (0.002% plus 0.1%) were prepared in a vehicle of 95% ethanol in propylene glycol (7:3 v/v) containing 0.5 mg butylated hydroxytoluene per ml of solution.

One hundred microliters ($\mu l$) of the test solutions were applied to 3×6 cm areas on buttock skin of normal healthy adults. Treatment sites were occluded with Saran brand plastic wrap, covered with a light-proof dressing and secured with surgical tape for 2 days. Epidermal biopsies were taken using a keratome device with a blade set at 0.2 mm to cut near the junction of epidermis-dermis. Thus, biopsies contained primarily epidermis with residual amount of dermis (approx. 10% maximum). Biopsies were snap-frozen immediately in liquid nitrogen. Total RNA was then isolated from the biopsies as described by Elder et al., Retinoic acid receptor gene expression in human skin, J. Invest Dermatol 96(4):425–33 (1991). 15 $\mu g$ RNA from each isolate was subjected to Northern blotting analysis as described in Xiao et al., in "Cloning, expression, and transcriptional properties of the human enhancer factor TEF-1", Cell 65(4):551–68 (1991). Human 24-hydroxylase cDNA fragments (Chen et al., "Isolation and expression of human 1,25-dihydroxyvitamin D3 24-hydroxylase cDNA", Proc Natl Acad Sci USA 90(10):4543–7 (1993)) were labeled with $\alpha$-[$^{32}$P]-dCTP (3000 Ci/mmole, DuPont-NEN, Boston, Mass.) using a random priming kit purchased from Boehringer Mannheim (Indianapolis, Ind.).

Figure 1:
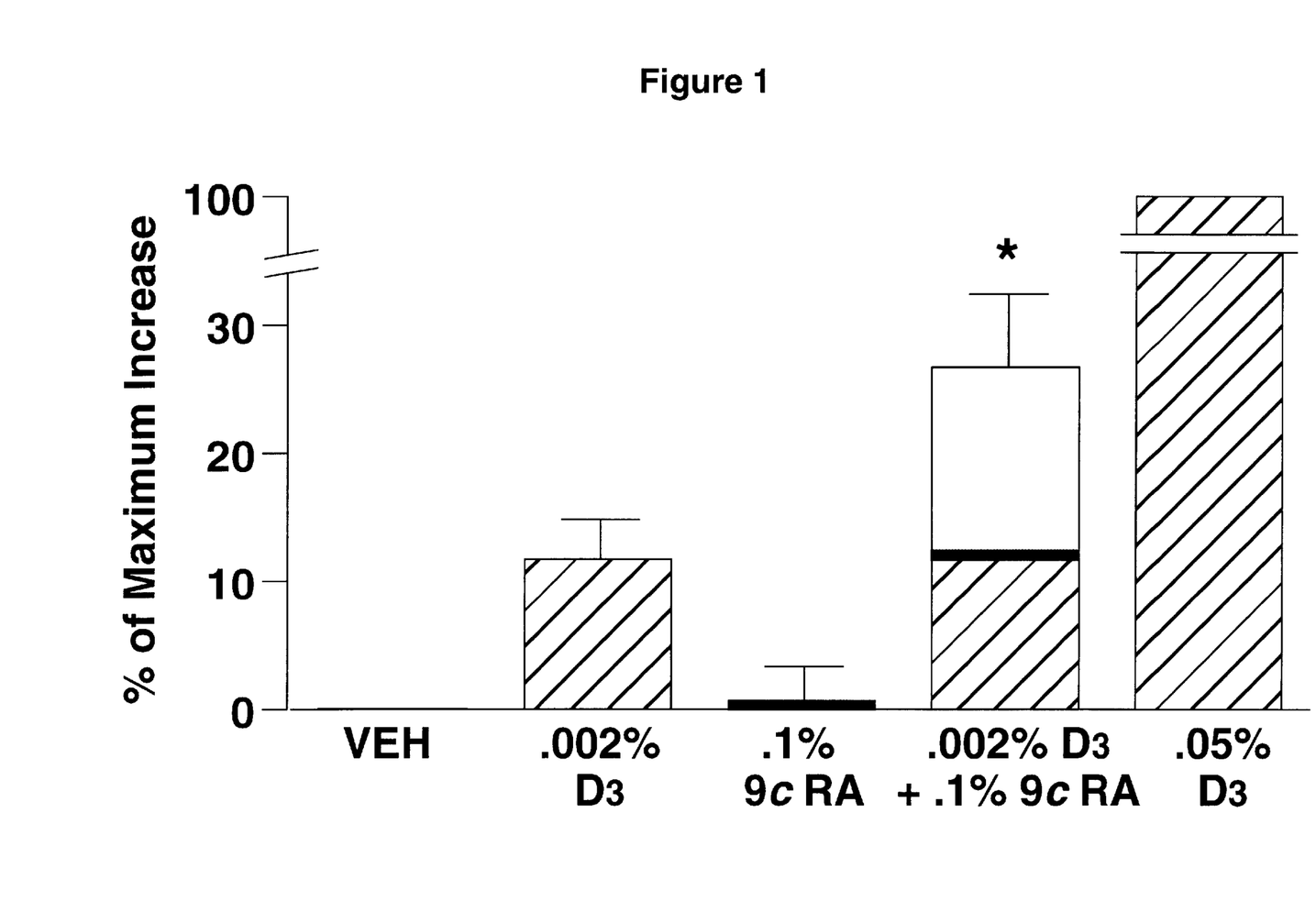
FIGS. 1–8 are depict result of testing described in the examples following in the specification.

FIG. 1 is a graph depicting the results of the Northern blots. In FIG. 1, the following abbreviations are used: VEH=vehicle; 9cRA=9-cis retinoic acid; D3 $1,25(OH)_2D_3$; 24-hydroxylase=24-OHase. As shown in FIG. 1, 0.002% D3 increased 24-OHase mRNA induction by 11% whereas 9cRA by itself yielded no significant increase. However, addition of 9cRA to 0.002% D3 together caused a synergistic 125% increase (relative to D3 alone) in 24-OHase mRNA induction.

Example 2

Effect on $1.25(OH)_2D_3$ In Skin of 24-Hydroxylase Inhibitor Topical Application Solutions of $1,25(OH)_2D_3$ (0.002%, 0.05%), ketoconazole (1%), and $1,25(OH)_2D_3$ plus ketoconazole (0.002%+1%) were prepared as described above.

Figure 2:
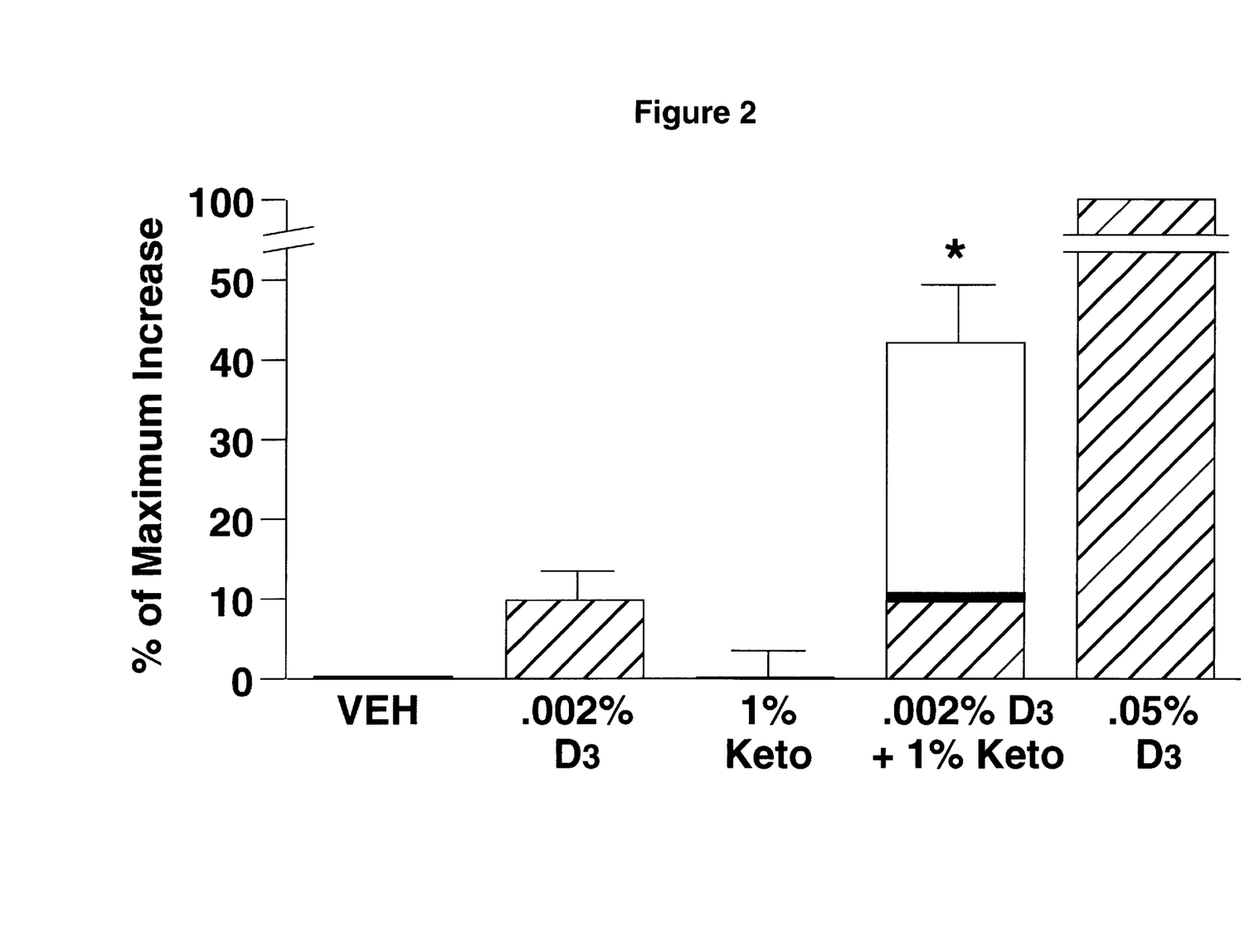

Skin was treated with these solutions and analyzed for 24-hydroxylase mRNA induction as described above. The results of these tests are shown in FIG. 2, in which Keto=ketoconazole. As shown in that Figure, D3 alone increased 24-OHase mRNA induction by approximately I 1% whereas ketoconazole treatment yielded no significant increase. However, the combination of D3 and keto acted synergistically to give a 320% increase (relative to D3 alone) in 24-OHase mRNA induction.

Example 3

Figure 3:
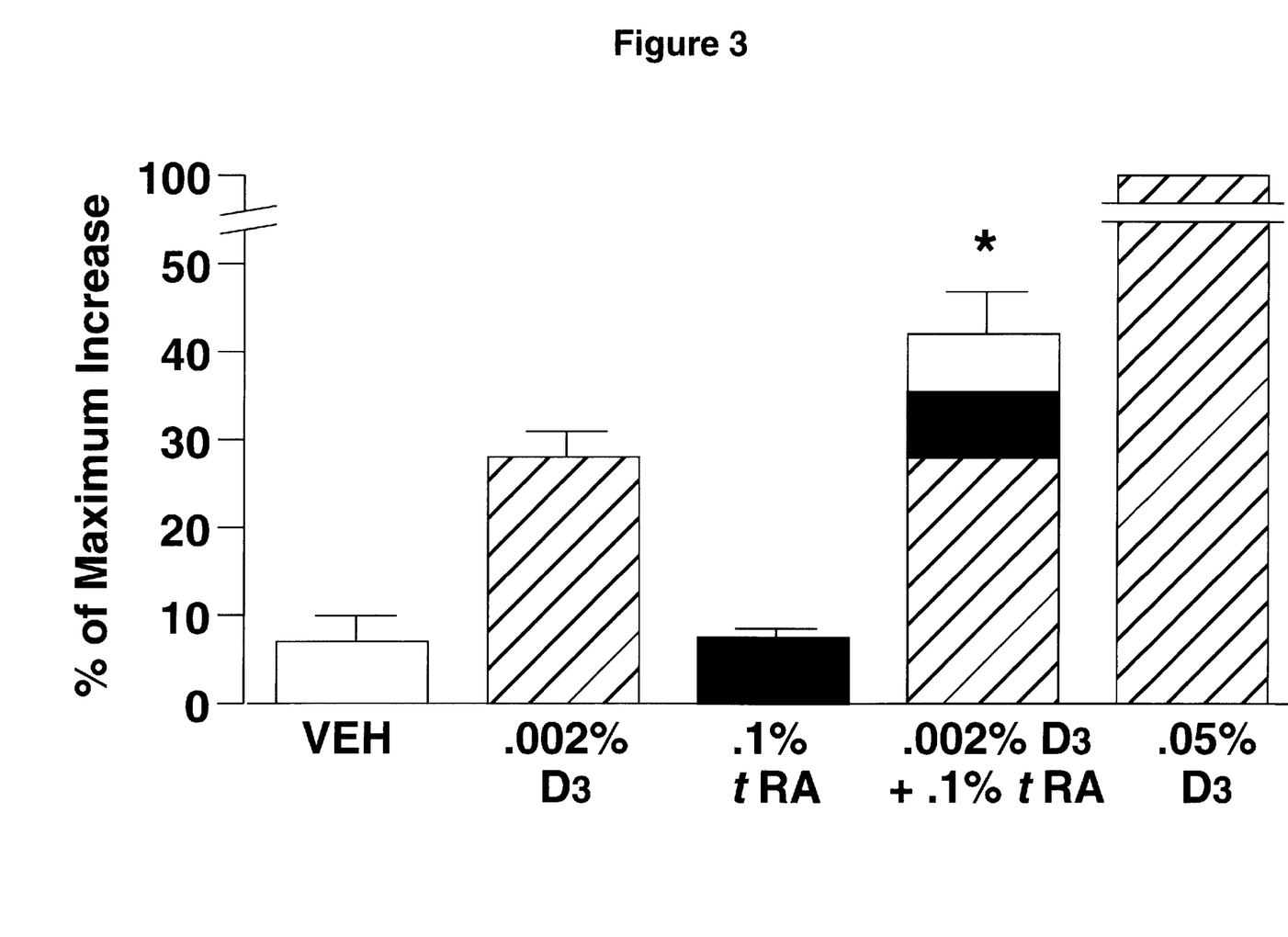

Determination of Effect on $1,25(OH)_2D_3$ Activity in Skin of All trans Retinoic Acid All trans retinoic acid is known to isomerize in skin to 9-cis retinoic acid. Solutions of D3, all trans retinoic acid (0.1%), and D3 plus all trans retinoic acid (0.002% plus 0.1%) were prepared as above. Skin was treated with those solutions and analyzed for 24-OHase mRNA induction as described above. The results of these tests are shown in FIG. 3, where tRA=all trans retinoic acid. As shown in FIG. 3, the combination of D3 and tRA yielded an increase in 24-OHase mRNA induction greater than would be expected from the increase caused by D3 alone and tRA alone.

Examples 4–8

The substance of the following examples is also described in the inventors' paper entitled "The Retinoid X Receptor Agonist 9-cis-Retinoic Acid and the 24-Hydroxylase Inhibitor Ketoconazole Increase Activity of 1,25-Dihydroxyvitamin $D_3$ in Human Skin In Vivo" in vol. 108 of *J. Invest. Dermatol.*, 1997 (the disclosure of which is incorporated herein by reference).

Materials $1,25(OH)_2D_3$, 25-hydroxyvitamin $D_3$ or cholecalciferol [$25OHD_3$], 24,25-dihydroxyvitamin $D_3$ [$24,25(OH)_2D_3$], 25,26-dihydroxyvitamin $D_3$ [$25,26(OH)_2D_3$], $1,24,25(OH)_3D_3$, 1,25,26-trishydroxyvitamin $D_3$ [$1,25,26(OH)_3D_3$], and 9-c-RA were obtained from Hoffmann La Roche (Nutley, N.J.). All-transretinoic acid (t-RA) was obtained from Sigma (St. Louis, Mo.). Ketoconazole powder was obtained from Johnson and Johnson (Skillman, N.J.) and Janssen Pharmaceutical (Beerse, Belgium). Deoxycytidine 5'-[$\alpha$-$^{32}$P] triphosphate and 25-[$^3$H]OHD$_3$ (25-OH[26,27-methyl-$^3$H] cholecalciferol) were obtained from DuPont-NEN (Boston, Mass.) and Amersham Life Science (Arlington Heights, Ill.), respectively.

Treatment of Subjects and Procurement of Tissue

Solutions of $1,25(OH)_2D_3$ (0.0004%, 0.002%, 0.01%, and 0.05%), 9-c-RA (0.1%), t-RA (0.1%), ketoconazole (1%), $1,25(OH)_2D_3$ plus 9-c-RA (0.002% and 0.1%, respectively), $1,25(OH)_2D_3$ plus t-RA (0.002% and 0.1%, respectively), and $1,25(OH)_2D_3$ plus ketoconazole (0.002% and 1%, respectively) were prepared in a vehicle comprising 95% ethanol and propylene glycol at 7:3 (vol/vol). Each solution also contained the anti-oxidant butylated hydroxytoluene (0.5 mg per ml). One hundred microliters of the study solutions were applied once to areas 3 cm×6 cm on buttock skin of normal healthy adults. Sites were occluded with Saran brand wrap and then covered with a tape-secured light-proof dressing for 2 days. For treatment with ketoconazole plus $1,25(OH)_2D_3$, the study sites were treated with the imidazole for 3 hours before application of the combination solution. Treated areas were infiltrated with 1% lidocaine local anesthesia and biopsied with a keratome ($\approx$150 µm thick). Keratomed specimens were immediately frozen in liquid nitrogen and stored at $-70°$ C. until used.

Measurement of 24-OHase mRNA

For measurement of 24-OHase mRNA, total cellular RNA was extracted from keratome biopsies obtained as described above. The guanidinium isothionate-cesium chloride procedure was used as described (Elder et al, 1990). RNA species (20 µg per sample) were electrophoretically size-fractionated on agarose gels and transferred to derivatized nylon membranes. The blots were sequentially hybridized against $^{32}$P-labeled 24-OHase cDNA and 36B4 (Åström et al, 1991). DNA probes were prepared by random priming (Boehringer Mannheim, Indianapolis, Ind.) and quantitated by using a PhosphorImager (Molecular Dynamics, Sunnyvale, Calif.) as described (Elder et al, 1990; Åström et al, 1991), except that 36B4 rather than cyclophilin was used as the control probe. Integrated autoradiographic intensity obtained by PhosphorImager for the 24-OHase gene was first divided by that of the control gene (36B4). The division product was then divided again by that of the control treatment for relative comparisons. Because the negative control (vehicle) group contained many small numbers, including zero, which precluded the required computations (division by zero), data are expressed as percent induction of the positive control (0.05% $1,25(OH)_2D_3$), which was considered maximum induction.

Measurement of 24-OHase Enzyme Activity

Human skin treated with vehicle and 0.05% $1,25(OH)_2D_3$ for 2 days under continuous occlusion was keratome-biopsied. The biopsy specimens were incubated in trypsin (0.1% in solution consisting of 30 mM HEPES buffer, 10 mM glucose, 3 mM KCl, 130 mM NaCl, and 1 mM sodium phosphate, pH 7.2) for 30 min at $35°$ C. to separate the epidermis from the dermis. Dispersed epidermal cells were centrifuged at 2000×g for 5 min. The pelleted cells were resuspended in 5 ml of 0.1% trypsin inhibitor and then centrifuged again at 2000×g for 5 min. The cells were washed twice with 5 ml of the digestion buffer (without trypsin). The final cell pellet was resuspended in 1 ml of enzyme assay buffer (20 mM HEPES buffer, 125 mM KCl, 20 mM succinate, 2 mM $MgCl_2$, 1 mM dithiothreitol and 1 mM ethylenediamine tetraacetic acid, pH 7.4). To 20 µl of resuspended cells, 1 µM 25-[$^3$H]OHD$_3$ (1 µCi) was added to start the reaction. When used, ketoconazole was added at a final concentration of $1×10^{-4}$ M. After a 30-min incubation at $35°$ C., the reaction was stopped with the addition of 2.6 ml of methanol:chloroform. 2:1 (vol/vol). After adding 1.2 ml of chloroform and 1 ml of water, the samples were vortex-mixed for 1 min and then allowed to separate into two layers. The aqueous layer was washed twice with 1.2 ml of chloroform. With each wash, the chloroform layer was pooled and then evaporated to dryness, and the material was resuspended in 200 µl of methanol. The material was filtered with Millipore SJHV 004 filters into high-performance liquid chromatography vials. After evaporation to dryness, the material was taken up in a final volume of 30 µl for high-performance liquid chromatography analysis.

High-Performance Liquid Chromatography Separation of Vitamin $D_3$ Metabolites

The standard solutions used to identify and quantitate vitamin $D_3$ metabolites were $25OHD_3$, $24,25(OH)_2D_3$, $1,25(OH)_2D_3$, $25,26(OH)_2D_3$, $1,24,25(OH)_3D_3$, and $1,25,26(OH)_3D_3$. Vitamin D3 metabolites were separated by using a Hewlett-Packard 1090M high-performance liquid chromatography system with a chem workstation, a pilot wavelength of 264 nm, and a Spherisorb ODSI column of 4.6×200 mm. An isocratic elution with 90% solvent A (acetonitrile) and 10% solvent B (0.005 M ammonium acetate:acetic acid. 100:1 (vol/vol)) was achieved with a flow rate of 0.7 ml/min at $26°$ C. for 22 minutes. The effluent from the column flowed directly into a Radiomatic model 295A flow through liquid scintillation spectrometer for quantitation of tritium in each of the separated metabolites.

Statistical Analysis

Comparisons of mean levels of 24-OHase mRNA among treated sites were made with either the paired t test or the repeated measures analysis of variance. All p values are two-sided. Summary statistics are expressed as means ±SEM. Data was performed with the use of the Michigan Interactive Data System (MIDAS) a statistical software package developed at the Center for Statistical Consultation and Research at the University of Michigan.

Results

24-OHase Gene Expression Is Induced by $1,25(OH)_2D_3$ in Human Skin

Figure 4:
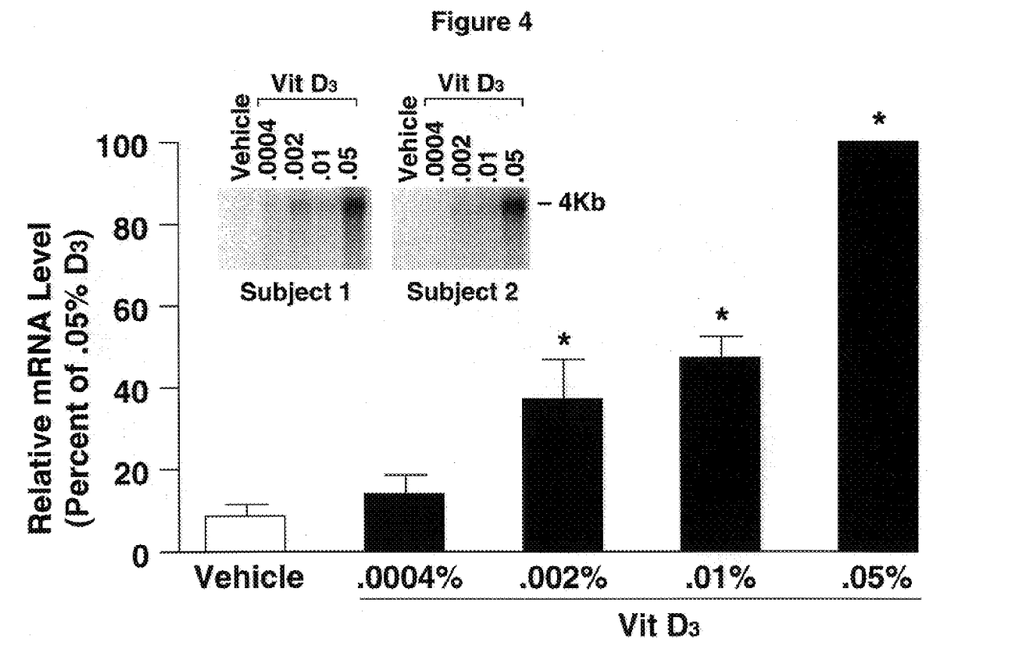

To determine whether the 24-OHase gene in human skin can be regulated in vivo by $1,25(OH)_2D_3$, four different concentrations of the hormone were applied once under occlusion for 48 hours. Northern blot analysis revealed a concentration-dependent induction of the 24-OHase mRNA levels, as shown in FIG. 4. In vehicle treated skin, the mRNA level was very low and detectable. For this reason, the data are expressed as fractions of the level observed with 0.05% $1,25(OH)_2D_3$, the highest concentration used, set arbitrarily at 100% (maximum induction). As compared with vehicle treatment, the application of 0.002% 1,25(OH)$_2$D$_3$ caused a small but statistically significant increase in the mRNA level. In the Northern Blot analysis shown in FIG. 4: * means p<0.05 versus vehicle (open bar); n=5; and the inset blots are from two representative subjects.

Figure 5:
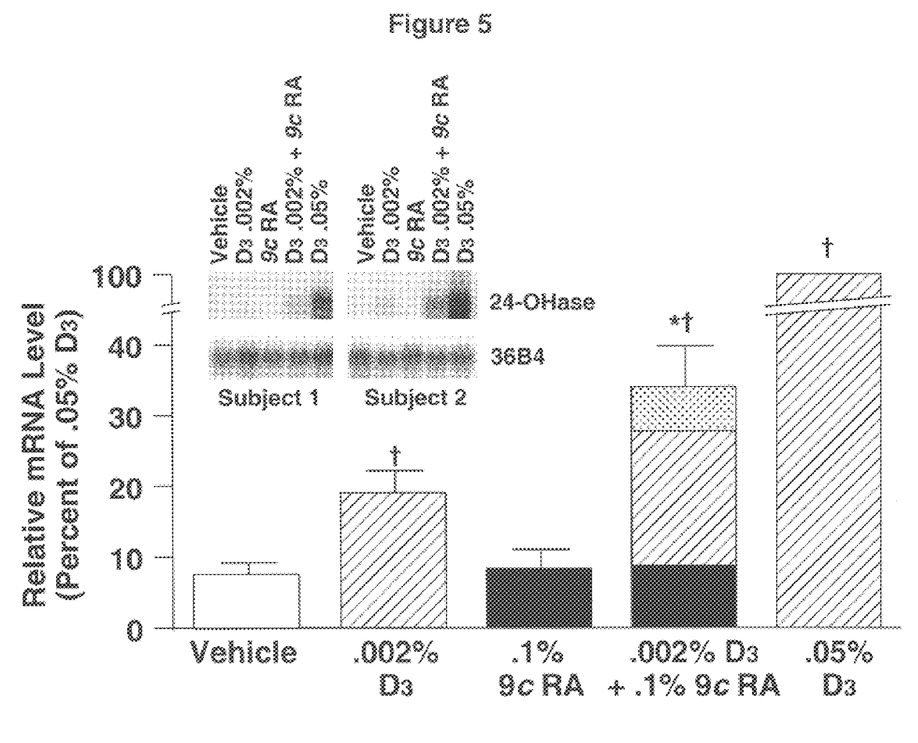

24-OHase Gene Expression by 1,25(OH)$_2$D$_3$ Is Synergistically Induced by 9-c-RA After determining the dose-response curve for 24-OHase mRNA induction by 1,25(OH)$_2$D$_3$ application, we investigated whether the small increase in 24-OHase mRNA caused by a low dose of 1,25(OH)$_2$D$_3$ (0.002%) could be augmented by the application of 9-c-RA. Compared with vehicle, 9-c-RA by itself did not change human epidermal 24-OHase gene expression after 48 h of occlusive treatment, as shown in FIG. 5. Similar to the results shown in FIG. 4, 0.002% 1,25(OH)$_2$D$_3$ alone induced a small but significant increase in 24-OHase mRNA level (18% of maximum; p<0.05 versus vehicle, n=15). Unexpectedly, however, when 0.002% 1,25(OH)$_2$D$_3$ was co-administered with 0.1% 9-c-PA, the combination caused a synergistic increase in mRNA levels to 33% of maximum. More particularly in FIG. 5: *p<0.05 versus 0.002% 1,25(OH)$_2$D$_3$; $^\dagger$p<0.05 versus vehicle, n=15; D$_3$ and 1,25(OH)$_2$D$_3$ are represented by the stripped hatching. The combination treatment (0.002% D$_3$ plus 0.1% 9-c-RA) has a bar height greater than the additive sum; the stippled hatching shows the synergistic effect. Again, the inset blots are results from two representative subjects.

Figure 6:
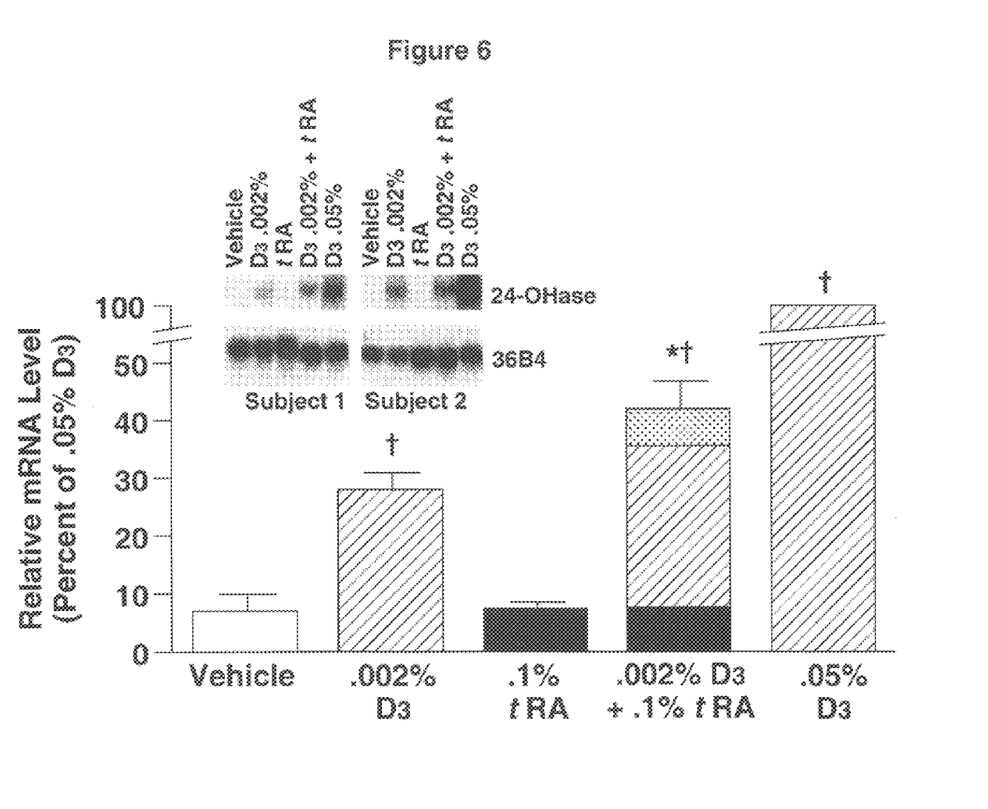

24-OHase Gene Expression by 1,25(OH)$_2$D$_3$ Is Synergistically Induced by t-RA We have demonstrated that after topical application of t-RA to human skin, its stereoisomers including 9-c-RA can be detected in the viable epidermis (Duell et al, 1996). Therefore, we next sought to determine whether concomitant treatment of 1,25(OH)$_2$D$_3$ with t-RA can enhance induction of 24-OHase mRNA, similar to that observed with 9-c-RA co-application. Two days of occlusive treatment with t-RA alone did not induce 24-OHase mRNA expression, as compared with vehicle, as shown in FIG. 6. Compared to 0.05% 1,25(OH)$_2$D$_3$ (maximum induction), 1,25(OH)$_2$D$_3$ enhanced the expression of 24-OHase mRNA by 28% (p<0.05 versus vehicle, n=15). In the presence of 0.1% t-RA, however, 0.002% 1,25(OH)$_2$D$_3$ treatment significantly induced the mRNA level to more than 40% of the level observed with 0.05% 1,25(OH)$_2$D$_3$. In FIG. 6: *p<0.05 versus 0.002% 1,25(OH)$_2$D$_3$; $^{554}$p<0.05 versus vehicle; n=15. As with FIG. 5, the stippled section of the combination treatment depicts the synergistic effect of the combination therapy, and the insets are from two representative subjects.

24-OHase Gene Expression by 1,25(OH)$_2$D$_3$ Enhanced by Ketoconazole

Figure 7:
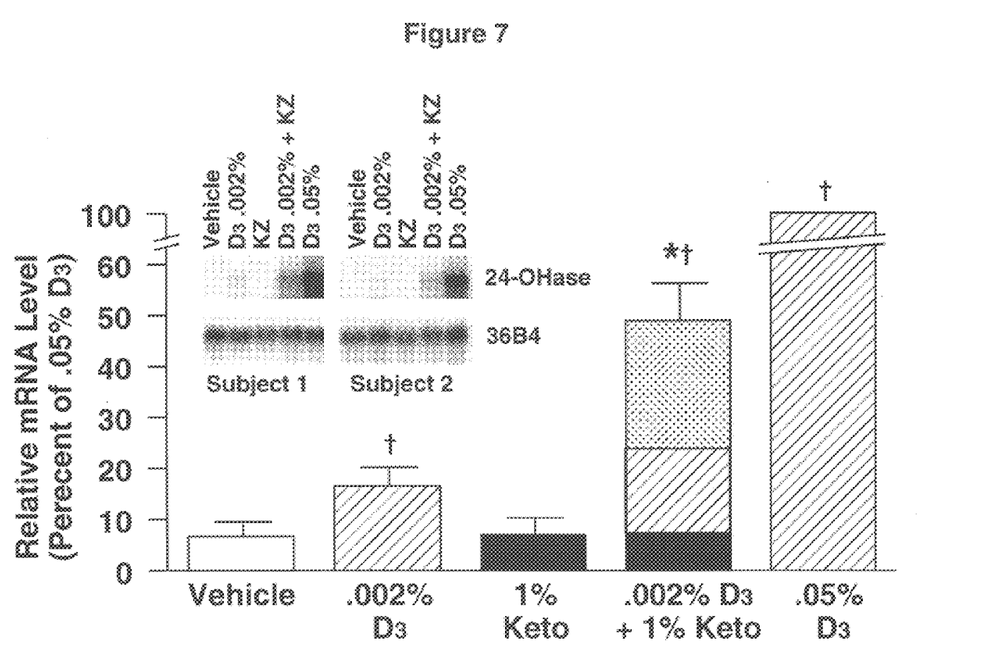

Ketoconazole is a dermatologically suitable imidazole known to inhibit several P-450 enzymes involved in hormone metabolism. It also possesses an inhibitory activity against retinoic acid 4-OHase, which inactivates t-RA (Duell et al., 1992). Inhibition of 4-OHase by liarozole, a related imidazole, augments human skin responses to low doses of retinoic acid and retinol (Kang et al. 1996). Ketoconazole can similarly influence vitamin D signaling in human skin by inhibiting the 24-OHase. To support this, the induction of 24-OHase mRNA by 1,25(OH)$_2$D$_3$ was examined in the presence of and in the absence of the ketoconazole. Consistent with previous examples presented herein, 0.002% 1,25(OH)$_2$D$_3$ alone caused a small but significant increase in the 24-OHase mRNA level as compared with vehicle (18% of maximum; p<0.05), as shown in FIG. 7. Ketoconazole at 1% alone did not alter the mRNA level. Ketoconazole, when combined with 0.002% 1,25(OH)$_2$D$_3$, however, synergistically increased the transcription level to approximately half of the maximal induction caused by 0.05% 1,25(OH)$_2$D$_3$, as shown in FIG. 7. In FIG. 7: *p<0.05 vs. 0.002% 1,25(OH)$_2$D$_3$; $^\dagger$p<0.05 vs. vehicle, n=5; again, the stippled pattern shows the enhanced benefits of combination therapy according to this invention.

Figure 8:
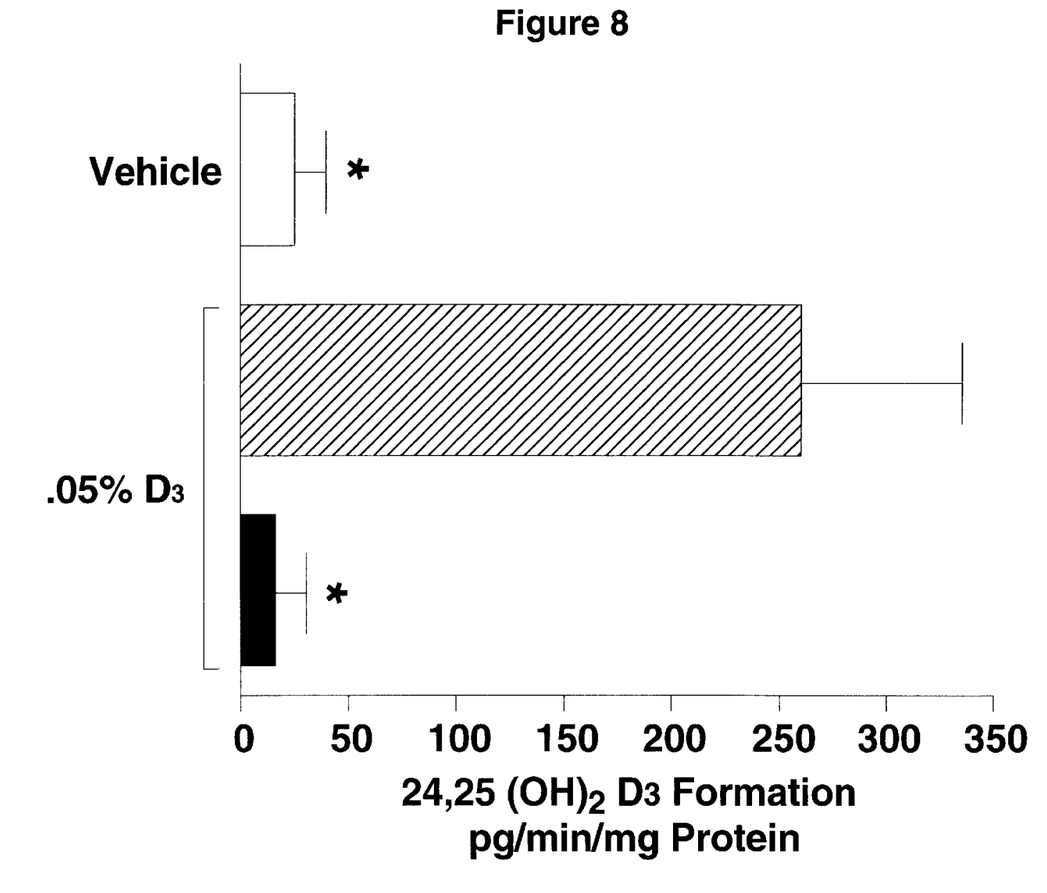

1,25(OH)$_2$D$_3$ Induces Human Epidermal 24-OHase Activity and Ketoconazole Inhibits the Induced 24-OHase Activity We studied the inducibility of the cytochrome P-450 enzyme activity in human skin in vivo by 0.05% 1,25(OH)$_2$D$_3$ occlusive treatment for 2 days to support the inhibition of 24-OHase by ketoconazole. Epidermal cells derived from vehicle- and 1,25(OH)$_2$D$_3$-treated sites were assayed for transformation of 25-OHD$_3$ to 24,25(OH)$_2$D$_3$. Compared to vehicle (25±15 pg per min per mg of protein), there was a 10-fold increase (p<0.05; n=5) in the formation of 24,25 (OH)$_2$D$_3$ by 1,25(OH)$_2$D$_3$ (260±78 pg per min per mg of protein) as shown in FIG. 8. This induced activity of 24-OHase by 1,25(OH)$_2$D$_3$ treatment was completely inhibited by addition of ketoconazole (1×10$^{-4}$ M) ex vivo, also shown in FIG. 8, in which the open bar is vehicle, the striped bar is 1,25(OH)$_2$D$_3$, and the solid bar is 1,25(OH)$_2$D$_3$ plus ketoconazole.

The concentration-dependent induction of 24-OHase mRNA expression by 1,25(OH)$_2$D$_3$ indicates that in human skin in vivo, the presence of only the VDR ligand is sufficient to activate the gene. The barely detectable 24-OHase mRNA levels in normal (vehicle treated) skin and the robust induction of this gene transcript by 1,25(OH)$_2$D$_3$ make this a useful bioassay to test for vitamin D activity of a compound in human skin in vivo. This appears analogous to cellular retinoic acid binding protein (CRABP)-II mRNA induction by topical retinoid application to human skin. Enhanced expression of this gene, whose far upstream promoter contains a retinoic acid-responsive element (Astr öm et al, 1991), by an occlusive treatment with natural or synthetic retinoids has predicted their retinoidal activity in human skin in vivo (Griffiths et al., 1993; Elder et al, 1995). The potential value of 24-OHase gene expression as a measure of vitamin D activity in human skin, however, is greater than that for CRABP-II mRNA induction for retinoids. This is because, although retinoids typically give dose dependent responses clinically (i.e., erythema) and/or histologically (i.e., hyperplasia of the epidermis), 1,25(OH)$_2$D$_3$ and its synthetic analog calcipotriene, which is currently in clinical use, do neither. Thus, induction of 24-OHase mRNA provides a detectable 1,25(OH)$_2$D$_3$ target in the absence of any appreciable clinical or histologic activity in human skin in vivo. Furthermore, this enhanced expression of 24-OHase by 1,25(OH)$_2$D$_3$ treatment correlates with an increase in 24-OHase enzyme activity.

The ability of 9-c-RA to synergistically enhance the 24-OHase mRNA level induced by a low dose of 1,25(OH)$_2$D$_3$ indicates that RXR is not a silent partner in RXR-VDR heterodimer complex-mediated vitamin D signaling in human skin in vivo. In cell culture, human keratinocytes from normal adults transfected with a reporter gene VDRE (DR3)-tk-CAT (where CAT is chloramphenicol acetyltransferase) demonstrated more than a doubling of chloramphenicol acetyltransferase activity when 9-c-RA was added to a low dose of 1,25(OH)$_2$D$_3$. This chloramphenicol acetyltransferase activity could be further increased by over-expressing VDR and/or RXR, in the transfected keratinocytes, which strongly indicates the direct contribution of the receptors to the ligand-mediated inducibility.

Although 9-c-RA is the only natural ligand of RXR identified to date, it is also an agonist of RARs (Heyman et at, 1992; Allenby et al, 1993). In addition, because 9-c-RA can isomerize to t-RA in human skin tissue (Duell et al, 1996), a contribution of RAR-VDR in vitamin D signaling after 9-c-RA and $1,25(OH)_2D_3$ co-treatment cannot be excluded. This is unlikely to be of major significance in human skin, however, because in epidermal nuclear extract preparations, we have not detected endogenous RAR-VDR heterodimers binding to VDREs. Furthermore, in our in vitro transfection system and in C57BL/6 adult mice in vivo, the use of RXR-specific ligand SR 11237 provided results that were comparable with that of 9-c-RA, synergistically enhancing 24-OHase mRNA induction by $1,25(OH)_2D_3$. The lack of adequate toxicology data to assure safe use in humans prevented us from applying this synthetic compound to humans (hence its application to mice).

Similar to 9-c-RA, t-RA synergistically enhanced 24-OHase mRNA induction with a low dose (0.002%) of $1,25(OH)_2D_3$. Compared to $1,25(OH)_2D_3$ treatment alone, addition of t-RA increased the transcription level by 50%, and 9-c-RA did so by 76% (p=0.74 vs 50% increase). The comparable magnitude of modest synergism caused by the two RA isomers with $1,25(OH)_2D_3$ is not inconsistent with RXR-VDR being the major heterodimer complex in vitamin D signaling in human skin in vivo. We have recently reported that the same 0.1% solution of t-RA applied to human skin for 48 h yielded approximately 7 nM 9-c-RA in the viable epidermis (Duell et al, 1996). Dissociation constant (Kd) values reported for 9-c-RA binding to RXRs have ranged from 11 to 18 nM (Heyman et al, 1992; Levin et al, 1992; Allenby et al, 1993). The Kd determination made with endogenous retinoid receptors (RXR and combined) in nuclear extracts from human epidermis, in which the level of RXR protein is 5-fold greater than that of RAR protein, was 1.2 nM (Fisher et al, 1994). Therefore, the 7 nM 9-c-RA that forms after 0.1% t-RA is likely sufficient to activate skin RXRs. Indeed, although 0.1% 9-c-RA treatment results in 260 nM 9-c-RA in stratum corneum-free epidermis (Duell et al, 1996), no significant difference in synergism with $1,25(OH)_2D_3$ was detected between 9-c-RA and t-RA (FIGS. 5–6).

Although both t-RA and 9-c-RA augmented vitamin D signaling, $1,25(OH)_2D_3$, at concentrations used in our study, did not increase or decrease the ability of t-RA or 9-c-RA to stimulate relevant target genes. When the blots were stripped of 24-OHase probes and reprobed with CRABP-II probes, we found, consistent with previous observations (Kang et al, 1995; Elder et al, 1996), that both t-RA and 9-c-PA markedly induced CRABP-II mRNA levels. Compared with a single treatment of t-RA or 9-c-RA, co-administration of each RA isomer with $1,25(OH)_2D_3$ did not influence the level of CRABP-II gene transcripts (data not shown).

In human skin in vivo, neither 9-c-RA nor t-RA alone induced 24-OHase mRNA expression. Similar results were obtained from cultured human keratinocytes and mouse skin in vivo. By contrast, in mouse kidney, systemic administration of both natural and synthetic ligands enhanced the expression of the 24-OHase gene without the presence of vitamin D3 (Allegretto d al. 1995). This apparent tissue-specific gene regulation indicates that, in addition to the receptors and their cognate ligands, other factors are involved in the process. The importance of relative ratios of VDR, and RXR, in determining the degree of ligand responsiveness (Lemon and Freeman, 1996) and the identity of the RXR isoform in influencing VDR heterodimer transactivation of the 24-OHase gene by $1,25(OH)_2D_3$ and 9-c-RA (Kephart et al. 1996) were recently demonstrated. It is also possible that as described for estrogen and thyroid hormone receptors (Chen and Evans, 1995; Horlein et al, 1995) co-activator and/or co-repressor proteins may be modulating VDR and RXR activities. Therefore, tissue-restricted expression of the receptors/receptor isoforms and/or co-activators/co-repressors may be responsible in part, for the differential response to ligands observed in skin and kidney.

Ketoconazole is a broad-spectrum P-450 inhibitor that has been used clinically in a variety of conditions ranging from fungal infections, seborrheic dermatitis, and psoriasis to prostatic carcinoma (Farr et al., 1985; Green et al, 1987; Mahler et al., 1993; Degreef and DeDoncker, 1994). Topically, ketoconazole has beer safely used as a 2% cream and shampoo formulations. We found 1% ketoconazole to be effective in synergistically increasing the 24-OHase mRNA level caused by a low dose of $1,25(OH)_2D_3$. The marked inhibition of $1,25(OH)_2D_3$-induced human epidermal 24-OHase activity by ketoconazole ex vivo (FIG. 8) implies that the synergism in vivo was achieved by impeding the inactivation of $1,25(OH)_2D_3$ by topical ketoconazole. By itself, however, application of ketoconazole did not induce 24-OHase mRNA expression. This is probably because, under in vivo conditions, an effective inhibition of 24-OHase activity by topical ketoconazole does not increase endogenous $1,25(OH)_2D_3$ to a level efficient to induce 24-OHase mRNA.

Our data indicate that vitamin D signaling in human skin in vivo can be significantly increased by two different mechanisms: RXR ligands and 24-OHase inhibitors. Although not specifically studied, RXR ligands will likely increase vitamin D signaling by synthetic compounds, such as calcipotriene, which can bind and transactivate target genes via VDR. Because the synergistic effects observed with 9-c-RA and ketoconazole are mediated by distinct pathways, a combination of both will likely lead to enhancement of the bioactivity of $1,25(OH)_2D_3$. Combination topical therapy with RXR agonist and/or 24-OHase inhibitor allows the use of less $1,25(OH)_2D_3$ than would be necessary when using $1,25(OH)_2D_3$ as a single agent, to deliver a desired biologic/therapeutic response to human skin. In principle, a reduction in the amount of applied $1,25(OH)_2D_3$ required to produce a pharmacologic effect would minimize potential risk of hypercalcemia.

While the present invention is described particularly with reference to human subjects, and includes in vivo evidence using human subjects, there are likely various veterinary utilities for the instant invention for other animals, especially mammals, exhibiting vitamin D metabolism analogous to that in human skin.

As described herein, the assays and testing methods were performed in vivo on human subjects (after informed consent). It should be understood that the invention herein is also applicable to methods performed on living skin tissue cultures and on matrices supporting living skin cells (as are used in the development of artificial skin).

The foregoing description is meant to be illustrative and not limiting. Various changes, modifications, and additions may become apparent to the skilled artisan upon a perusal of this specification, and such are meant to be within the scope and spirit of the invention as defined by the claims.

What is claimed is:

1. A composition for the topical treatment of a dermatological condition, comprising:
    (a) 1,25(OH)$_2$D$_3$ or an analog thereof, or a mixture thereof; and (b) an RXR ligand or a precursor of an RXR ligand or a mixture thereof,
    wherein the combined amount of said 1,25(OH)$_2$D$_3$ and said analog and said mixture thereof in said composition is ineffective alone for said treatment, and which combined amount is effective in combination with said RXR ligand or precursor or mixture thereof.

2. The composition of claim 1, wherein said RXR ligand is selected from the group consisting of retinoic acid and precursors thereof.

3. The composition of claim 2, wherein the retinoid is 9-cis-retinoic acid.

4. The composition of claim 2, wherein the precursor is all trans-retinoic acid.

5. The composition of claim 1, further comprising a 24-hydroxylase inhibitor in addition to said RXR ligand.

6. The composition of claim 5, wherein the 24-hydroxylase inhibitor is ketoconazole.

7. The composition of claim 1, wherein the precursor is all trans retinoic acid, and the 24-hydroxylase inhibitor is ketoconazole.

8. The composition of claim 1, comprising about 0.002% to about 0.05% by weight of 1,25(OH)$_2$D$_3$.

9. The composition of claim 1, comprising about 0.025% to about 0.1% by weight of RXR ligand.

10. A composition for the topical treatment of a dermatological condition, comprising:
    (a) 1,25(OH)$_2$D$_3$, an analog thereof, or a mixture thereof, which is metabolized by 24-hydroxylase; and (b) a 24-hydroxylase inhibitor or a mixture thereof;
    wherein the combined amount of said 1,25(OH)$_2$D$_3$ and said analog and mixture thereof in said composition is ineffective alone for said treatment, and which combined amount is effective in combination with said 24-hydroxylase inhibitor or said mixture thereof.

11. The composition of claim 10, wherein the 24-hydroxylase inhibitor is ketoconazole.

12. The composition of claim 10, further comprising an RXR ligand.

13. The composition of claim 12, wherein the RXR ligand is all-trans retinoic acid or 9-cis retinoic acid.

14. The composition of claim 13, wherein the 24-hydroxylase inhibitor is ketoconazole.

15. The composition of claim 10, comprising about 0.002% to about 0.05% by weight of 1,25(OH)$_2$D$_3$.

16. The composition of claim 1, comprising about 1% to about 3% by weight of RXR ligand.

* * * * *